United States Patent
Wadgaonkar et al.

(10) Patent No.: US 9,950,996 B2
(45) Date of Patent: Apr. 24, 2018

(54) BIO-BASED AROMATIC DIISOCYANATES FOR PREPARATION OF POLYURETHANES

(71) Applicant: Council of Scientific & Industrial Research, New Delhi (IN)

(72) Inventors: Parakash Purushottam Wadgaonkar, Maharashtra (IN); Sachin Suresh Kuhire, Maharashtra (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/539,189

(22) PCT Filed: Dec. 23, 2015

(86) PCT No.: PCT/IN2015/050214
§ 371 (c)(1),
(2) Date: Jun. 23, 2017

(87) PCT Pub. No.: WO2016/103283
PCT Pub. Date: Jun. 30, 2016

(65) Prior Publication Data
US 2017/0369427 A1    Dec. 28, 2017

(30) Foreign Application Priority Data

Dec. 23, 2014 (IN) .......................... 3866/DEL/2014

(51) Int. Cl.
| | | |
|---|---|---|
| *C07C 263/12* | (2006.01) | |
| *C07C 247/24* | (2006.01) | |
| *C08G 18/77* | (2006.01) | |
| *C08G 18/32* | (2006.01) | |
| *C08G 18/24* | (2006.01) | |
| *C08G 71/04* | (2006.01) | |
| *C07C 265/14* | (2006.01) | |

(52) U.S. Cl.
CPC .......... *C07C 263/12* (2013.01); *C07C 247/24* (2013.01); *C08G 18/246* (2013.01); *C08G 18/3206* (2013.01); *C08G 18/771* (2013.01); *C08G 71/04* (2013.01); *C07C 265/14* (2013.01)

(58) Field of Classification Search
None
See application file for complete search history.

(56) References Cited

U.S. PATENT DOCUMENTS 4,597,910 A    7/1986 Konig et al.

OTHER PUBLICATIONS

Nohra et al. "From Petrochemical Polyurethanes to Biobased Polyhydroxyurethanes", Macromolecules, vol. 46, No. 10, May 28, 2013, p. 3771-3792.

*Primary Examiner* — Jafar Parsa
*Assistant Examiner* — Amy C Bonaparte
(74) *Attorney, Agent, or Firm* — Blank Rome LLP

(57) ABSTRACT

The present invention provides bio-based aromatic diisocyanate of formula (I). [Formula should be inserted here] wherein X is $OCH_3$, Y is selected from —H or $OCH_3$, and m=0-12. The present invention further provides a method for preparation of aromatic diisocyanate of formula (I) useful for preparation of polyurethane.

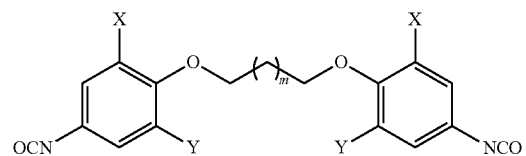

9 Claims, 2 Drawing Sheets

| Polyurethane | l | X | Y |
|---|---|---|---|
| PU-1 | 10 | -H | -OCH₃ |
| PU-2 | 12 | -H | -OCH₃ |
| PU-3 | 10 | -OCH₃ | -OCH₃ |
| PU-4 | 12 | -OCH₃ | -OCH₃ |

BIO-BASED AROMATIC DIISOCYANATES FOR PREPARATION OF POLYURETHANES

RELATED APPLICATIONS

This application is a national phase of PCT/IN2015/050214, filed on Dec. 23, 2015 which claims priority to 3866/DEL/2015 filed Dec. 23, 2014. The content of those applications are hereby incorporated by reference.

FIELD OF THE INVENTION

The present invention relates to bio-based aromatic diisocyanates of formula (I) useful for preparation of polyurethanes. Particularly the present invention relates to process of preparation of bio-based aromatic diisocyanates wherein the starting materials are derived from bio-resources. More particularly the present invention further relates to preparation of polyurethane from bio-based aromatic diisocyanates of formula (I).

BACKGROUND OF THE INVENTION

Polyurethanes are a versatile class of polymers which find applications in elastomers, foams, coating, biomedical devices, etc. The principal monomers for synthesis of polyurethanes are diol/polyol and diisocyanates. Usually, hydroxyl-terminated prepolymers or aliphatic diols and diisocyanates such as toluenediisocyanate, methylene bis(phenyl isocyanate), hexamethylene diisocyanate, etc are used. The starting materials for synthesis of polyurethanes are mostly derived from fossil resources. Recent research efforts are directed towards synthesis of diols/polyols and diisocyanates based on renewable resource materials. Several examples of diols/polyols and aliphatic diisocyanates derived from bio-based chemicals are known in the literature. However, examples of aromatic diisocyanates based on bio-derived chemicals are scarce. Still et al. in Macromolecular Chemistry and Physics, Volume 185, Pages 697-707, Journal 1984 disclose synthesis of renewable furan-based diisocyanate.

Lignin is one of the most abundant aromatic renewable resource and is a by-product of various industries like sugarcane industry, paper and pulp mills. Utilization of lignin-based aromatic building blocks for the synthesis of monomers is of great interest. Recently, Pang et al. in Polymer Chemistry. Volume 5, Page 2843, Journal 2014 reported aliphatic-aromatic polyesters from lignin-derived chemicals. Mialon et al. in US patent no US 2013/0137847 A1. 2013 disclosed bio-renewable PET mimic derived from lignin-based aromatics. Caillol et al. in Green Chemistry, Volume 16, Page 1987, Journal 2014 reported a library of monomers starting from vanillin, which in turn is obtained from lignin.

Wadgaonkar et al. in European Polymer Journal, Volume 71, Page 547, Journal 2015 reported aliphatic-aromatic polyurethanes and in WO patent no WO 2015/140818 A1 disclosed pendant furyl containing bisphenols starting from lignin-based aromatics.

It would be advantageous to provide novel aromatic diisocyanates from bio-based starting materials. Such diisocyanates find applications in polyurethane industries.

Korean Pat. No. KR20130056025 discloses manufacturing method of polyurethane resin comprising the steps of 1) a mixture obtained by mixing poly(tetramethylene glycol) (PTMG), poly(carbonate diol), 1,3-propandiol, 1,4-butandiol, 2,2-bis(hydroxyl methyl) propionic acid(DMPA) as a diol/polyols and dibutyltin dilaurate(DBTDL) as a catalyst; 2) Prepolymer was synthesized by reaction of diisocyanate with mixture of diol/polyols and catalyst; 3) Polyurethane resin was synthesized by adding a chain extender into the prepolymer mixture. Chain extender was selected from EDA(ethylenediamine), DETA(diethylene tri amine).

Chinese Pat. No. CN103030969 discloses waterborne polyurethane curing agent and its preparation method. Polyurethane curing agent is made by using polyisocyanate (46-77%), polyether polyol (3.5-17.2%), phosphoric acid (01-0.05%), DBTDL (0.01-0.3%) and solvent such as N,N-dimethylformamide at a temperature of 65° C.-100° C. for 3-6 h.

Korean Pat. No. KR20030049684 discloses polymeric resin composition for water curable filler and process for producing polyurethane using the same composition. The process for producing polyurethane comprises the step of agitating polyisocyanate (mixed polyisocyanate containing MDI and isophorone diisocyanate in the ratio of 4:1) with the polymeric resin composition for water curable fillers in the ratio of 1:1 at a high speed. The polymeric resin composition for water curable fillers comprises 30 to 100 wt % of greeno13001, 0.1 to 5 wt % of TEDA, 5 to 30 wt % of DPG(1000, 750, 280), 0.1 to 5 wt % of DBTDL, 5 to 30 wt % of DMEA, 0.1 to 5 wt % of B8404, 1 to 10 wt % of $H_2O$, 8 to 28 wt % of $CaCO_3$, 1.4 to 8.5 wt % of 1,4-butanediol, 1.8 to 30 wt % of ethylene oxide, and 10 to 40 wt % of glycerol.

PCT Pat. Appl. No. WO2011123492 discloses a method of making polyurethane dispersions made from a mixture of aromatic polyisocyanates including: (1) forming a polyurethane prepolymer from a composition including: a) at least one polyol; b) at least one diol containing carboxyl functionality; c) an isomeric mixture of diphenylmethyl diisocyanate including about 37% by weight or less of 4,4'-methylene bis (phenyl isocyanate); and optionally, but desirably, d) at least one additional aromatic isocyanate and (2) combining the polyurethane prepolymer from step (1) with at least one neutralizing amine and water. DBTDL is also used.

Article titled "Preparation and characterization of waterborne polyurethane crosslinked by urea bridges" by Hercule et al. published in *International Journal of Chemistry*, 2011, 3 (2), pp 88-96 reports waterborne polyurethane dispersion were prepared by polyaddition reaction using polyethylene glycol (PEG Mw 2000) and isophorone diisocyanate (IPDI) in presence of dibutyltin dilaurate (DBTL) as catalyst.

Article titled "Catalytic activity of DBTDL in polyurethane formation" by Niyogi Sobhan et al. published in *Indian Journal of Chemical Technology*, 2002, 9, pp 330-333 reports preparation of Polyurethane from neopentyl glycol (NPG) and toluene diisocyanate (TDI) using dibutyltin dilaurate (DBTDL) catalyst.

OBJECTIVE OF THE INVENTION

The main objective of the present invention is to provide a bio-based aromatic diisocyanate of formula (I) useful for synthesis of polyurethane.

Another objective of the present invention is to provide a process of preparation of aromatic diisocyanate of formula (I).

Still another objective of the present invention is to provide a process of preparation of polyurethane from aromatic diisocyanate of formula (I).

SUMMARY OF THE INVENTION

Accordingly the present invention provides a bio-based aromatic diisocyanate of formula (I)

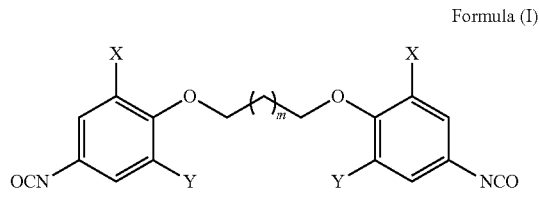

Formula (I)

wherein
X is —OCH$_3$, Y is selected from —H or —OCH$_3$, and m=0-12.

In an embodiment, the present invention provides an aromatic diisocyanate selected from
bis(4-isocyanato-2-methoxyphenoxy)alkane (Ia)

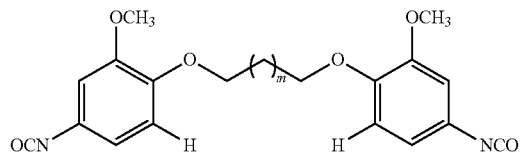

or
bis(4-isocyanato-2,6-dimethoxyphenoxy) alkane (Ib)

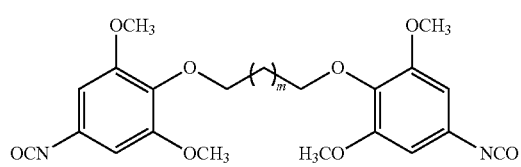

wherein m=0-12 in both Ia and Ib.

In another embodiment, the present invention provides a process for preparation of aromatic diisocyanate of formula (I)

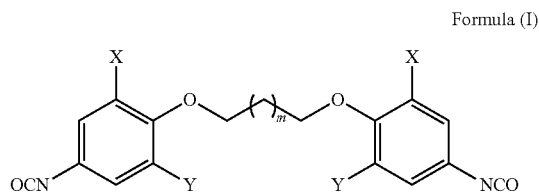

Formula (I)

wherein
X is —OCH$_3$, Y is selected from —H or —OCH$_3$, and m=0-12,
comprising the steps of:
(a) converting a bio-based phenolic acid to the corresponding methyl ester;
(b) converting the methyl ester of step (a) to an aromatic diester by etherification with dihaloalkane;
(c) hydrolyzing the aromatic diester of step (b) to the corresponding aromatic diacid;
(d) converting the aromatic diacid of step (c) to an aromatic diacyl azide; and
(e) converting the aromatic diacyl azide by thermal Curtius rearrangement to obtain corresponding aromatic diisocyanate of formula (I).

In still another embodiment of present invention, the bio-based phenolic acid used in step (a) of the process is selected from the group consisting of syringic acid and vanillic acid.

In still another embodiment of present invention, the syringic acid and vanillic acid are bio-derived.

In still another embodiment of present invention, the aromatic diisocyanate of formula (I) is useful for preparation of polyurethane, wherein process for the preparation of polyurethane comprises the steps of:
a) heating a reaction mixture of diisocyanate of formula (I), a diol or a polyol and a catalyst in a dry solvent in an inert atmosphere at a temperature in the range of 70° C. to 80° C. for a time period in range of 10 to 12 h; and
b) removing the solvent under reduced pressure to obtain the polyurethane.

In still another embodiment of present invention, said diol is bio-derived and selected from the group consisting of 1,3-propane diol, 1,10-decanediol, 1,12-dodecanediol; and said polyol is petroleum based and selected from the group consisting of polyethylene glycol (PEG) and poly(tetramethylene ether)glycol (PTMG).

In still another embodiment of present invention, the catalyst used is dibutyltin dilaurate (DBTDL).

In still another embodiment of present invention, the solvent used is selected from the group consisting of toluene, 1,4 dioxane, tetrahydrofuran, N N-dimethylacetamide, N N-dimethylformamide and N-methyl pyrrolidone.

In still another embodiment of present invention, the polyurethane obtained has a molecular weight in the range of $3.21 \times 10^4$ to $5.85 \times 10^4$.

DETAILED DESCRIPTION OF THE INVENTION

The present invention provides novel aromatic diisocyanates of formula (I).

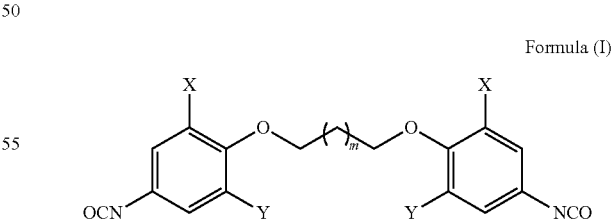

Formula (I)

wherein
X is —OCH$_3$, Y is selected from —H or —OCH$_3$
m=0-12.

A series of bio-based aromatic diisocyanates, namely, bis(4-isocyanato-2-methoxyphenoxy)alkane and bis(4-isocyanato-2,6-dimethoxyphenoxy) alkanes are synthesized from vanillic acid/syringic acid and dihaloalkanes which have their origin in bio-derived alkane diols. Lignin derived aromatic chemicals are used for the first time for synthesis of fully bio-based aromatic diisocyanates.

The method of preparation of novel diisocyanate of formula (I) comprising the following steps:
(a) Converting the substituted phenolic-acid to the corresponding methyl ester;
(b) Converting methyl ester of step (a) to aromatic diester by etherification with dihaloalkane;
(c) Hydrolyzing the aromatic diester of step (b) to the corresponding aromatic diacid;
(d) Converting the aromatic diacid of step (c) to an aromatic diacyl azide; and
(e) Converting the aromatic diacyl azide to obtain corresponding aromatic diisocyanate by thermal Curtius rearrangement.

Figure 1:
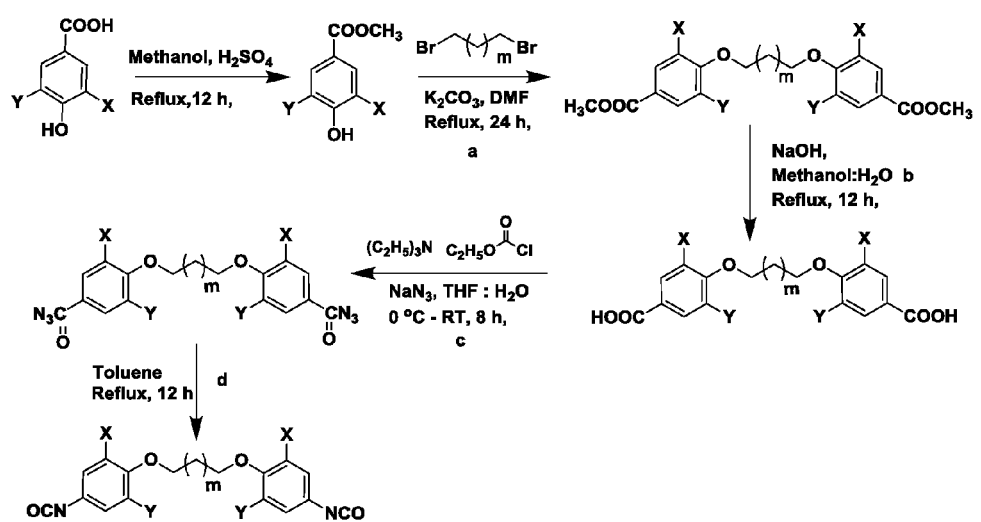
FIG. 1 depicts synthesis of aromatic diisocyanates containing oxyalkylene linkages and alkoxy substituents on aromatic rings.

The above process is shown in FIG. 1.

The method for preparation of polyurethane from bio-based aromatic diisocyanate of formula (I) comprising the following steps:
a) Heating a reaction mixture of diisocyanate of formula (I), a diol/polyol and a catalyst in a dry solvent in an inert atmosphere at a temperature in the range of 70° C. to 80° C. for 10 to 12 h; and
b) Removing the solvent under reduced pressure to afford the polyurethane.

The diol is selected from the group consisting of 1,3-propane diol, 1,10-decanediol, 1,12-dodecanediol, polyethylene glycol (PEG) and polytetramethylene ether glycol (PTMG).

The catalyst used is dibutyltin dilaurate (DBTDL).

The solvent used is selected from the group consisting of toluene, 1,4 dioxane, tetrahydrofuran, N N-dimethylacetamide, N N-dimethylformamide and N-methylpyrrolidone.

Figure 2:
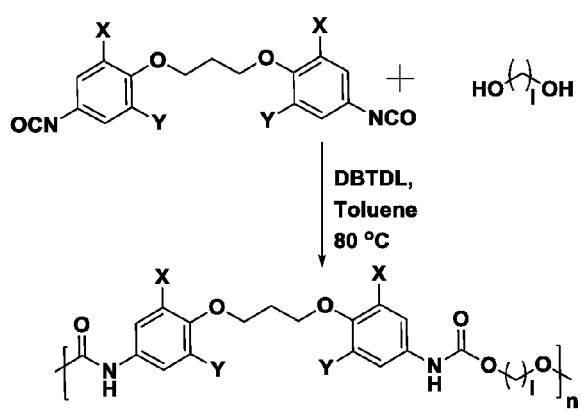
FIG. 2 depicts synthesis of polyurethanes.

The above process is shown in FIG. 2.

Polyurethane synthesized from aromatic diisocyanate exhibited number average molecular weight in the range of $3.21 \times 10^4$ to $5.85 \times 10^4$.

EXAMPLES

Following examples are given by way of illustration therefore should not be construed to limit the scope of the invention.

Example 1

A. General Procedure for Synthesis of Aromatic Diesters (2)

Into a 250 mL two-necked round bottom flask equipped with a reflux condenser were placed, methyl vanillate/syringate (80 mmol), anhydrous potassium carbonate (44.2 g, 320 mmol) and dry N,N-dimethylformamide (150 mL). The reaction mixture was heated at 100° C. for 1 h and then 1,3-dibromopropane (8.04 g, 40 mmol) was added dropwise. The heating was continued at 100° C. for 11 h. After completion of reaction (TLC), the reaction mixture was poured into ice cold water (500 mL) The solid product was collected by filtration and the solid was dissolved in dichloromethane (300 mL). The dichloromethane solution was washed with water (2×100 mL), dried over anhydrous sodium sulfate, filtered, and concentrated in a vacuo. The crude product was purified by silica gel column chromatography.

a) Synthesis of dimethyl 4,4'-(propane-1,3-diylbis(oxy))bis(3-methoxybenzoate)

Yield: 80%; M.P.-158° C.; $^1$H NMR (200 MHz, CDCl$_3$, δ/ppm): 2.35-2.48 (m, 2H), 3.90 (s, 6H), 4.30 (t, 2H), 6.94 (d, 2H), 7.54 (d, 2H), 7.64 (dd, 2H). $^{13}$C NMR (50 MHz, CDCl$_3$, δ/ppm): 28.9, 52.0, 56.0, 65.4, 111.5, 112.3, 122.8, 123.4, 148.9, 152.2, 166.8 b) Synthesis of dimethyl 4,4'-(propane-1,3-diylbis(oxy))bis(3,5-dimethoxybenzoate)

Yield: 76%; M.P.-110° C.; $^1$H NMR (200 MHz, CDCl$_3$, δ/ppm): 2.12-2.24 (m, 2H), 3.83 (s, 12H), 3.91 (s, 6H), 4.30 (t, 4H), 7.27 (s, 4H); $^{13}$C NMR (50 MHz, CDCl$_3$, δ/ppm): 31.0, 52.2, 56.1, 70.7, 106.7, 124.9, 141.5, 153.1, 166.8

B. General Procedure for Synthesis of Aromatic Diacids (3)

Into a 250 mL two-necked round bottom flask equipped with a reflux condenser were placed, dimethyl 4,4'-(propane-1,3-diylbis(oxy))bis(3-methoxybenzoate)/dimethyl 4,4'-(propane-1,3-diylbis(oxy))bis(3,5-dimethoxybenzoate) (30 mmol), sodium hydroxide (12 g, 300 mmol), methanol (100 mL) and water (100 mL). The reaction mixture was refluxed for 12 h. After completion of reaction, the excess methanol was removed under reduced pressure. The solution was diluted with water and acidified with aqueous hydrochloric acid (3M). The precipitated solid was filtered and dried under vacuum at 60° C. for 4 h. The product was recrystallized from aqueous ethanol.

a) Synthesis of 4,4'-(propane-1,3-diylbis(oxy))bis(3-methoxybenzoic acid)

Yield=90%; M.P.-259° C.; $^1$H NMR (200 MHz, DMSO-d$_6$, δ/ppm): 7.54 (dd, 2H), 7.44 (d, 2H), 7.08 (d, 2H), 4.19 (t, 4H), 3.79 (s, 6H), 2.19-2.25 (m, 2H); $^{13}$C NMR (50 MHz, DMSO-d$_6$, δ/ppm) 167.1, 151.8, 148.4, 123.2, 123.1, 112.1, 112.0, 65.0, 55.5, 28.5 b) Synthesis of 4,4'-(propane-1,3-diylbis(oxy))bis(3,5-dimethoxybenzoic acid)

Yield=92%; M.P.-266° C.; $^1$H NMR (200 MHz, DMSO-d$_6$, δ/ppm): 12.93 (br.s, 2H), 7.21 (s, 4H), 4.13 (t, 4H), 3.79 (s, 12H), 1.92-2.01 (m, 2H); $^{13}$C NMR (50 MHz, DMSO-d$_6$, δ/ppm): 167.0, 152.7, 140.5, 125.7, 106.4, 69.8, 55.9, 30.6

C. General Procedure for Synthesis of Aromatic Diacyl Azides (4)

Into a 250 mL two-necked round bottom flask equipped with a reflux condenser, an argon inlet and an addition funnel were charged, aromatic dicarboxylic acids (20 mmol) and a mixture of tetrahydrofuran:water (3:1 v/v) (100 mL). The reaction mixture was cooled to 0° C. and a solution of triethyl amine (12 g, 120 mmol) in tetrahydrofuran (20 mL) was added dropwise over a period of 15 min. To the reaction mixture, ethylchloroformate (12.8 g, 120 mmol) was added dropwise over a period of 10 min and stirred for 2 h. A solution of sodium azide (7.8 g, 160 mmol) in water (30 mL) was added dropwise over a period of 10 min and mixture was stirred for 2 h at 0° C. then for 4 h at room temperature. Ice cold water (250 mL) was added gradually to the reaction mixture and solid was precipitated out. The precipitate was filtered and washed with water. Then the product was dissolved in dichloromethane and washed with water (150 mL), dried over anhydrous sodium sulfate, filtered, and concentrated in under reduced pressure at 25° C. to afford a white product.

a) Synthesis of 4,4'-(propane-1,3-diylbis(oxy))bis(3-methoxybenzoyl azide)

Yield=78.2%; M.P.-114° C.; IR (KBr): v=2140, 1680 cm$^{-1}$; $^1$H NMR (200 MHz, CDCl$_3$, δ/ppm): 7.66 (dd, 2H), 7.51 (d, 2H), 6.93 (d, 2H), 4.31 (t, 2H), 3.90 (s, 6H), 2.36-2.48 (m, 2H); $^{13}$C NMR (50 MHz, CDCl$_3$, δ/ppm): 171.6, 153.6, 149.2, 123.9, 123.4, 111.8, 111.7, 65.3, 56.0, 28.8; HRMS (ESI): m/z calculated for C$_{19}$H$_{18}$N$_6$O$_6$ (M+Na), 449.1180; found, 449.1162.

b) Synthesis of 4,4'-(propane-1,3-diylbis(oxy))bis(3,5-dimethoxybenzoyl azide)

Yield=81%; M.P.-110° C.; IR (KBr): v=2146, 1684 cm$^{-1}$; $^1$H NMR (200 MHz, CDCl$_3$, δ/ppm): 7.25 (s, 4H), 4.32 (t, 4H), 3.83 (s, 12H), 2.11-2.24 (m, 2H); $^{13}$C NMR (50 MHz, CDCl$_3$, δ/ppm): 171.8, 153.1, 143.0, 125.3, 106.6, 70.7, 56.1, 31.1; HRMS (ESI): m/z calculated for C$_{21}$H$_{22}$N$_6$O$_8$ (M+Na), 509.1391; found, 509.1393.

D. General Procedure for Synthesis of Aromatic Diisocyanate (5)

Into a 100 mL two-necked round bottom flask equipped with a reflux condenser and a nitrogen inlet were charged, aromatic diacyl azides (4.69 mmol) and dry toluene (25 mL) The reaction mixture was heated at 80° C. for 8 h. The toluene was removed under reduced pressure at 60° C. and white solid compound was obtained.

a) Synthesis of 1,3-bis(4-isocyanato-2-methoxyphenoxy)propane

Yield=83%; M.P.-136° C.; IR (KBr): v=2292 cm$^{-1}$; $^1$H NMR (400 MHz, CDCl$_3$, δ/ppm): 6.84 (d, 2H), 6.63 (dd, 4H), 4.21 (t, 4H), 3.83 (s, 6H), 2.27-2.39 (m, 2H); $^{13}$C NMR (50 MHz, CDCl$_3$, δ/ppm): 150.0, 146.4, 126.5, 124.2, 116.6, 113.9, 108.8, 66.0, 56.0, 29.2; HRMS (ESI): m/z calculated for C$_{19}$H$_{18}$N$_2$O$_6$ (M+H), 371.1238; found, 371.1249.

b) Synthesis of 1,3-bis(4-isocyanato-2,6-dimethoxyphenoxy)propane

Yield=87%; M.P.-105° C.; IR (KBr): v=2268 cm$^{-1}$; $^1$H NMR (400 MHz, CDCl$_3$, δ/ppm): 6.31 (s, 4H), 4.16 (t, 4H), 3.79 (s, 12H), 2.12-2.19 (m, 2H); $^{13}$C NMR (50 MHz, CDCl$_3$, δ/ppm): 153.8, 153.4, 128.8, 102.2, 70.9, 56.1, 30.8; HRMS (ESI): m/z calculated for C$_{21}$H$_{22}$N$_2$O$_8$ (M+Na), 453.1268; found, 453.127.

Example 2

General Procedure for Synthesis of Poly(Ether Urethane)s

Into a 100 mL two-necked round bottom flask equipped with a reflux condenser and a nitrogen inlet were charged, aromatic diisocyanate (4.69 mmol), aliphatic diol (4.69 mmol), DBTDL (3×10$^{-3}$ mmol) and dry toluene (25 mL). The reaction mixture was heated at 80° C. for 8 h. The toluene was removed under reduced pressure at 60° C. and polymer was obtained. The polymer was dissolved in N,N-dimethylacetamide, precipitated in methanol, filtered and dried in vacuum oven at 40° C. for 12 h.

a) Synthesis of poly(ether urethane)s based on 1,3-bis(4-isocyanato-2-methoxyphenoxy)propane and 1,10-decanediol IR (KBr): v=3328, 1733, 1700 cm$^{-1}$; $^1$H NMR (200 MHz, DMSO-d$_6$, δ/ppm): 9.37 (s, 2H), 7.17 (d, 2H), 6.84-6.95 (m, 4H), 4.03 (t, 8H), 3.69 (s, 6H), 1.9-2.13 (m, 2H), 1.52-1.62 (m, 4H), 1.18-1.30 (m, 12H); $^{13}$C NMR (50 MHz, DMSO-d$_6$, δ/ppm): 153.6, 152.9, 135.2, 131.8, 96.0, 69.9, 64.1, 55.6, 30.4, 28.9, 28.7, 28.5, 25.3.

b) Synthesis of poly(ether urethane)s based on 1,3-bis(4-isocyanato-2-methoxyphenoxy)propane and 1,12-dodecanediol IR (KBr): v=3331, 1732, 1609 cm$^{-1}$; $^1$H NMR (200 MHz, DMSO-d$_6$, δ/ppm): 9.37 (s, 2H), 7.16 (d 2H), 6.88 (dd, 4H), 4.02 (t, 8H), 3.68 (s, 6H), 2.0-2.10 (m, 2H), 1.20-1.58 (m, 20H); $^{13}$C NMR (100 MHz, DMSO-d$_6$, δ/ppm): 153.7, 149.1, 143.3, 133.1, 114.2, 110.1, 103.8, 65.6, 64.0, 55.4, 29.0, 28.7, 25.4 c) Synthesis of poly(ether urethane)s based on 1,3-bis(4-isocyanato-2,6-dimethoxyphenoxy)propane and 1,10-decanediol IR (KBr): v=3335, 1730, 1705 cm$^{-1}$; $^1$H NMR (500 MHz, DMSO-d$_6$, δ/ppm): 9.45 (s, 2H), 6.82 (s, 4H), 4.04 (t, 4H), 3.93 (t, 4H), 3.67 (s, 12H), 1.86-1.91 (m, 2H), 1.56-1.61 (m, 4H), 1.25-1.33 (m, 12H); $^{13}$C NMR (125 MHz, DMSO-d$_6$, δ/ppm): 153.7, 152.9, 135.2, 131.8, 96.0, 69.9, 64.1, 55.6, 30.4, 28.9, 28.7, 28.5, 25.4 d) Synthesis of poly(ether urethane)s based on 1,3-bis(4-isocyanato-2,6-dimethoxyphenoxy)propane and 1,12-dodecanediol IR (KBr): v=3332, 1733, 1702 cm$^{-1}$; $^1$H NMR (400 MHz, DMSO-d$_6$, δ/ppm): 9.44 (s, 2H), 6.82 (s, 4H), 4.03 (t, 4H), 3.93 (t, 4H), 3.67 (s, 12H), 1.86-1.90 (m, 2H), 1.54-1.60 (m, 4H), 1.21-1.29 (m, 18H); $^{13}$C NMR (100 MHz, DMSO-d$_6$, δ/ppm): 153.6, 152.9, 135.2, 131.7, 96.0, 69.9, 64.1, 55.6, 29.0, 28.7, 28.6, 25.4

TABLE 1

Inherent viscosity, molecular weight and thermal properties of polyurethanes.

| Polyurethane | $\eta_{inh}$ (dL/g)$^a$ | GPC$^b$ | | | Tg (° C.)$^c$ | T$_{10}$ (° C.)$^d$ |
| --- | --- | --- | --- | --- | --- | --- |
| | | $M_n$ | $M_w$ | $M_w/M_n$ | | |
| PU-1 | 0.60 | 36100 | 62500 | 1.7 | 55 | 304 |
| PU-2 | 0.65 | 45500 | 88200 | 1.9 | 49 | 304 |
| PU-3 | 0.58 | 32100 | 51800 | 1.6 | 74 | 308 |
| PU-4 | 0.68 | 58500 | 100300 | 1.7 | 66 | 306 |

$^a$= $\eta_{inh}$ was measured with 0.5% (w/v) solution of poly(ether urethane)s in CHCl$_3$ at 30 ± 0.1° C.
$^b$= Measured by GPC in DMF, polystyrene was used as the calibration standard.
$^c$= Measured by DSC on second heating scan with heating rate at 10° C. min$^{-1}$ under nitrogen atmosphere
$^d$= Temperature at which 10% weight loss was observed under nitrogen atmospheres.

Advantages of Invention

Aromatic diisocyanates derived from bio-based starting materials
Bio-based polyurethanes obtained

We claim:
1. A bio-based aromatic diisocyanate of formula (I)

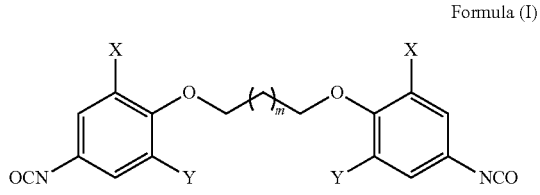

Formula (I)

wherein
X is —OCH₃, Y is —H or —OCH₃, and
m=0-12.

2. The aromatic diisocyanate as claimed in claim 1, wherein said diisocyanate is
-bis(4-isocyanato-2-methoxyphenoxy)propane

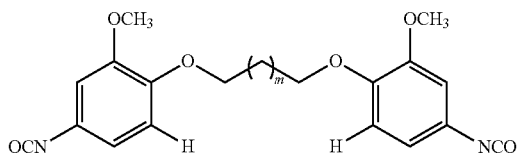

or
-bis(4-isocyanato-2,6-dimethoxyphenoxy)propane

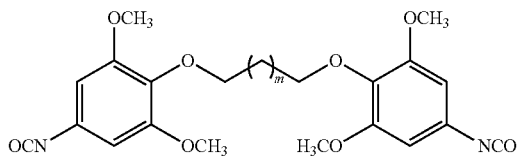

wherein m=1 in both 1a and 1b.

3. A process for the preparation of an aromatic diisocyanate of formula (I)

Formula (I)

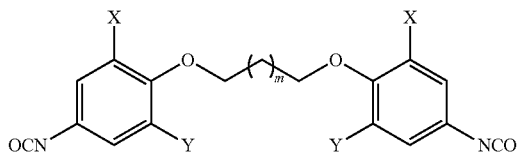

wherein
X is —OCH₃, Y is —H or —OCH₃, and
m=0-12,
comprising the steps of:
(a) converting a bio-based phenolic acid to the corresponding methyl ester;
(b) converting 2 equivalents of the methyl ester of step (a) to an aromatic diester by etherification with a dihaloalkane;
(c) hydrolyzing the aromatic diester of step (b) to the corresponding aromatic diacid;
(d) converting the aromatic diacid of step (c) to an aromatic diacyl azide; and
(e) converting the aromatic diacyl azide by thermal Curtius rearrangement to obtain the corresponding aromatic diisocyanate of formula (I).

4. The process as claimed in claim 3, wherein the bio-based phenolic acid used in step (a) is selected from the group consisting of syringic acid and vanillic acid.

5. The aromatic diisocyanate as claimed in claim 1, wherein the aromatic diisocyanate of formula (I) is useful for the preparation of a polyurethane, and wherein the process for the preparation of a polyurethane comprises the steps of:
a) heating a reaction mixture of a diisocyanate of formula (I), a diol or a polyol and a catalyst in a dry solvent in an inert atmosphere at a temperature in a range of 70° C. to 80° C. for a time period in a range of 10 to 12 h; and
b) removing the solvent under a reduced pressure to obtain the polyurethane.

6. The aromatic diisocyanate as claimed in claim 5, wherein said diol is bio-derived and is 1,3-propane diol, 1,10-decanediol, or 1,12-dodecanediol; and said polyol is petroleum based and is polyethylene glycol or poly(tetramethylene ether)glycol.

7. The aromatic diisocyanate as claimed in claim 5, wherein said catalyst is dibutyltin dilaurate (DBTDL).

8. The aromatic diisocyanate as claimed in claim 5, wherein said solvent is toluene, 1,4 dioxane, tetrahydrofuran, N N-dimethylacetamide, N,N-dimethylformamide, or and N-methyl pyrrolidone.

9. The aromatic diisocyanate as claimed in claim 5, wherein the polyurethane obtained has a molecular weight in the range of $3.21 \times 10^4$ g/mol to $5.85 \times 10^4$ g/mol.

* * * * *